United States Patent [19]

Hojeibane

[11] Patent Number: 5,125,896
[45] Date of Patent: Jun. 30, 1992

[54] STEERABLE ELECTRODE CATHETER

[75] Inventor: Hikmat J. Hojeibane, Charlestown, Mass.

[73] Assignee: C. R. Bard, Inc., Murray Hill, N.J.

[21] Appl. No.: 595,467

[22] Filed: Oct. 10, 1990

[51] Int. Cl.⁵ .................................... A61M 37/00
[52] U.S. Cl. ............................. 604/95; 128/786
[58] Field of Search ............. 604/95, 96, 264, 280, 604/281; 128/642, 658, 657, 772, 786

[56] References Cited

U.S. PATENT DOCUMENTS

| | | |
|---|---|---|
| 3,521,620 | 7/1970 | Cook . |
| 3,552,384 | 1/1971 | Pierie et al. . |
| 3,749,086 | 7/1973 | Kline et al. . |
| 3,773,034 | 11/1973 | Burns et al. . |
| 3,906,938 | 9/1975 | Fleischhaker . |
| 4,748,986 | 6/1988 | Morrison et al. . |
| 4,920,980 | 5/1990 | Jackowski . |
| 4,960,134 | 10/1990 | Webster, Jr. . |
| 4,960,411 | 10/1990 | Buchbinder ............... 604/95 |

Primary Examiner—John D. Yasko
Attorney, Agent, or Firm—Darby & Darby

[57] ABSTRACT

A steerable catheter comprising a hollow outer tube, a pair of coaxially aligned inner tubes disposed within a distal end portion of the outer tube, an actuating mechanism disposed at a proximal end of the outer tube, and a pull wire extending through the inner tubes from the distal end portion of the outer tube to the proximal end of the catheter. The actuating means includes a bushing slidable in the axial direction of the outer tube for tensioning the pull wire to thereby bend the distal end portion of the outer tube. A flat wire is disposed within the outer tube and is secured to the outer surface of the inner tubes to limit the direction of bending of the distal end portion. The catheter further includes a plurality of electrodes disposed at the distal end portion and connected by wires to an external monitor.

19 Claims, 1 Drawing Sheet

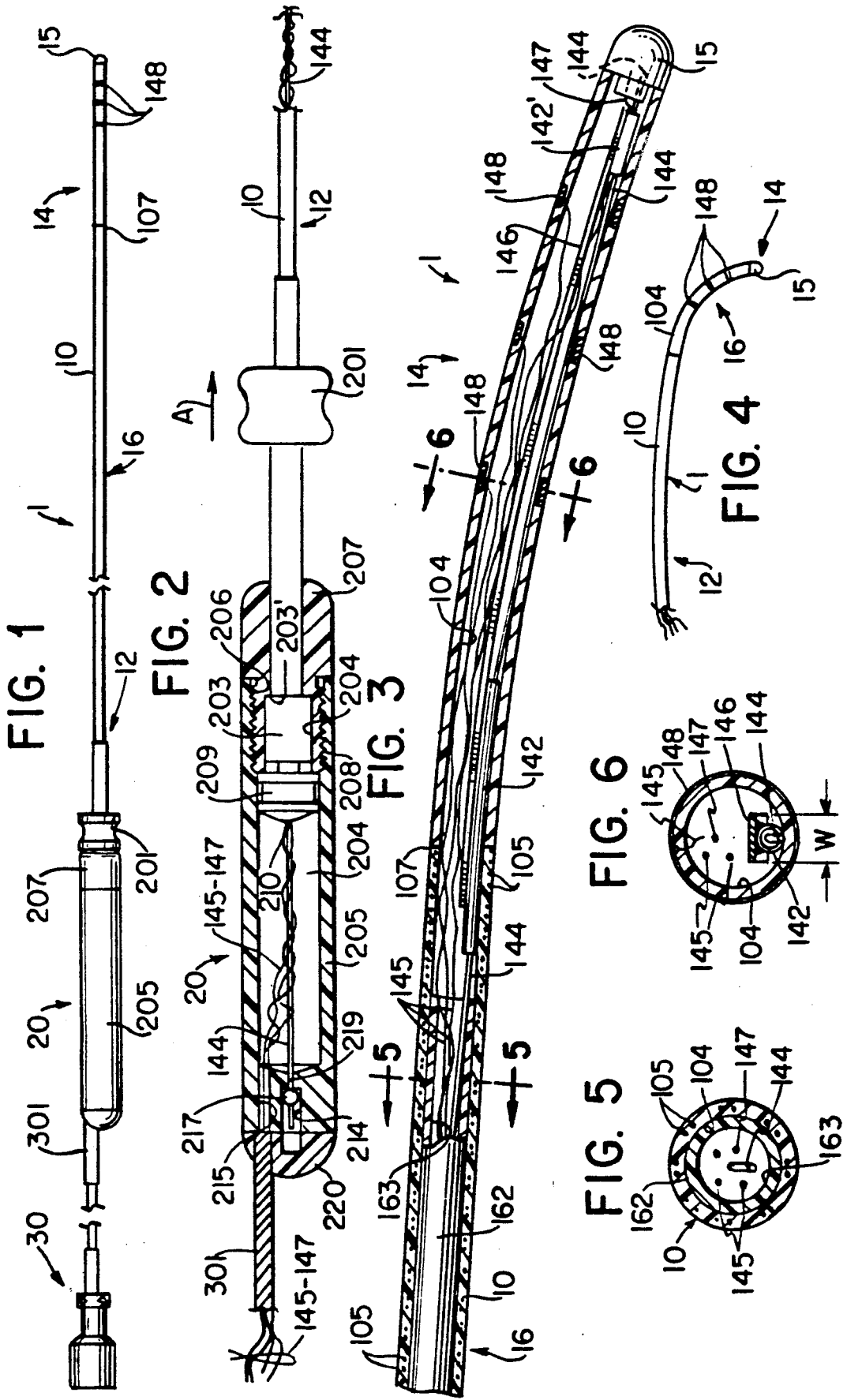

STEERABLE ELECTRODE CATHETER

BACKGROUND OF THE INVENTION

1. Field of the Invention

This invention relates to a catheter and, more particularly, to an electrode catheter having a remotely curvable tip.

2. Description of the Related Art

The advantages of steerable catheters are known. Such catheters are inserted into a blood vessel or other body area and their distal end guided in various directions to reach areas of the body which would otherwise be inaccessible. Examples of steerable catheters are disclosed in U.S. Pat. Nos. 3,749,086 to Kline et al.; 3,773,034 to Burns et al., 3,552,384 to Pieric and 3,521,620 to Cook.

A steerable catheter should have both flexibility for steering the catheter tip and rigidity to control steering. Known prior art catheters have been unable to successfully combine these two characteristics, tending instead to sacrifice one of these characteristics at the expense of the other. It is also desirable to limit the direction of bending of the distal end of the catheter to provide better steering control.

Catheters having electrode means for monitoring parts of the body, such as the heart, by transmitting electrical signals for analysis on an external monitor are also known. Currently a need exists for an electrode catheter which is steerable to access areas of the heart which could not be reached by a non-bendable catheter. It would be desirable to provide an electrode catheter with a steerable tip that combines sufficient flexibility to allow steering of the catheter to desired areas with good torsional rigidity and steering control.

SUMMARY OF THE INVENTION

According to the invention, an improved steerable electrode catheter comprises a hollow outer tube, first and second inner tubes disposed within the outer tube, actuating means disposed at the proximal end of the outer tube, and a pull wire extending through the inner tubes and secured to the distal end portion of the catheter. The actuating means is slidable distally to displace the outer tube towards the distal end, thereby tensioning the pull wire and causing the distal end portion to bend. A flat wire is disposed within the outer tube and is secured to an outer surface of the inner tubes, parallel to the pull wire, to limit bending of the distal end portion of the outer tube in a direction perpendicular to the flat wire. The catheter also includes a plurality of electrodes at the distal end portion to transmit electrical signals from the location in the body, such as the heart, to an external monitor.

BRIEF DESCRIPTION OF THE DRAWINGS

The objects, features and advantages of the present invention will be more fully appreciated as the same becomes better understood from the following detailed description of the present invention when considered in connection with the accompanying drawings, in which:

FIG. 1 is a side view showing the steerable catheter of the present invention;

FIG. 2 is a longitudinal sectional view showing the actuating mechanism of the steerable catheter of the present invention;

FIG. 3 is a longitudinal sectional view of the distal end portion of the catheter shown in a bent position;

FIG. 4 is a view of a catheter showing the distal end curved;

FIG. 5 is a cross section view taken along lines 4—4 of FIG. 3; and

FIG. 6 is a cross sectional view taken along lines 5—5 of FIG. 3.

DETAILED DESCRIPTION OF THE PREFERRED EMBODIMENT

Referring now to the drawings, wherein like reference numerals represent identical or corresponding parts throughout the several views, FIG. 1 shows the steerable catheter of the present invention designated generally by reference numeral 1. The catheter 1 can be used in a variety of applications, such as for cardiac treatment and diagnostic procedures. The catheter's steerability advantageously enables it to reach around curves or grooves and access narrow areas of the body, such as in the regions of the heart, which would otherwise not be accessible.

The catheter 1 of the present invention comprises a hollow outer tube 10 connected to an actuating mechanism 20. Reference numeral 30 designates generally the plug connection which joins the catheter 1 to an external monitor (not shown) for analyzing the region of the body in which the catheter is inserted.

Catheter 1 has a distal end portion 14 terminating in a distal electrode tip 15. Electrode tip 15 and distal end portion 14 are designed to be inserted into an area of a body such as an arterial blood vessel. A proximal end portion 12 and a central portion 16 connect the distal end portion 14 to the activating mechanism 20. It should be understood that the designation of these portions is for convenience of description only. Portion 14 is preferably composed of a soft material, and electrode tip 15 terminates in a hemispherically shaped region, thereby preventing puncturing of arterial (or other) walls.

Outer tube 10 has a central bore 104 extending through substantially its entire length. Central portion 16 and proximal end portion 12 of outer tube 10 are reinforced by a wire braid 105 (FIG. 5). The junction between the stiff wire braided area and the softer flexible distal portion 14 is designated in FIG. 3 by reference numeral 107. Although the outer tube 10 is shown as a single tube having a portion reinforced, alternatively, the reinforced portion can be in the form of a separate tube having a wire braid embedded therein which is welded to a flexible tube positioned at the distal end. In either embodiment, the reinforced portion provides rigidity to restrict bending of the proximal and central portions 12, 16 of the outer tube 10, thereby allowing only distal end portion 14 to flex.

Disposed within outer tube 10 is a pull wire 144 to induce bending of the catheter, a pair of inner tubes 142, 142' to retain pull wire 144, and a flat supporting wire 146 to restrict the direction of bending of the catheter. Inner tubes 142 and 142' are disposed within central bore 104 of outer tube 10 in the distal end portion 14. These inner tubes are disposed in approximate coaxial alignment and are spaced apart from one another so that the longer tube 142 is positioned proximally of the shorter tube 142'. Inner tubes 142 and 142' are spaced from the inner wall of outer tube 10 when outer tube 10 is in its straight position shown in FIG. 1.

Inner tubes 142, 142' are advantageously positioned and dimensioned to provide the desired curve for the distal end portion 14 when steering the catheter. Preferably, short inner tube 142' terminates slightly proximally of the distal tip electrode 15. Long tube 142 is positioned across junction 107 to provide for gradual transition in tensile strength of outer tube 10. That is, long tube 142 provides a progressive decrease in rigidity towards the distal tip 15, to thereby prevent breaking or snapping of the distal end portion 14 when steering the catheter. Tubes 142 and 142' also maintain the pull wire 144 on one side of a flat wire 146, the purpose of which is described below. In a preferred embodiment, the length of short tube 142' is approximately 0.5 cm, the length of long tube 142 is approximately 2.5 cm and it extends from approximately 1 cm proximal to junction 107. Of course, the inner tubes 142, 142' can be of other lengths as long as they achieve their function of allowing bending of the catheter and of retaining pull wire 144 as described below. The inner tubes 142, 142' are preferably composed of polyimide; however, other materials can be used as long as they have the same mechanical characteristics.

As shown in FIGS. 2 and 3, pull wire 144 is disposed longitudinally within bore 104 of outer tube 10 and is anchored at its distal end to the distal electrode 15 to direct the catheter to its desired position. Pull wire 144 extends the entire length of bore 104 through a housing of the actuating mechanism 20 so that its proximal end is anchored to a proximal portion of the mechanism in a manner described below. Pull wire 144 passes through the central openings of both inner tubes 142, 142' and is consequently retained therein and maintained on one side of flat wire 146. The tensioning of pull wire 144 causes the distal end portion 14 of outer tube 10 to bend from a straight position shown in FIG. 1 to a bent position illustrated in FIG. 4, which will be described in more detail below.

Flexible flat wire 146, preferably rectangular in cross section, is disposed longitudinally within bore 104 of outer tube 10, substantially parallel to pull wire 144 and inner tubes 142, 142', to limit the bending direction of the distal end portion 14 of the catheter 1 to one plane. The flat wire 146 extends through a substantial length of the distal end portion 14 of outer tube 10, its distal end terminating just proximally of the distal electrode 15. The proximal end of flat wire 146 terminates proximally of junction 107. In one embodiment, the length of flat wire 146 is 8 cm, its width is approximately 1 mm, and it is coated with an insulating material to prevent shorts between electrodes. Each of the inner tubes 142, 142' is secured to the bottom illustrated surface of flat wire 146 at the positions depicted in FIG. 3, preferably by adhesive, although other means of attachment can be utilized. Thus, flat wire 146 limits flexing of distal end portion 14 to a direction perpendicular to the large surface of wire 146 to thereby control steering.

Catheter 1 is provided with a plurality of electrodes, preferably made of platinum, at its distal end portion 14. The electrodes are electrically connected to a cable which feeds into a monitor for analysis of the part of the body in which the catheter 1 is inserted. For example, the electrodes can provide information regarding electrical signals within the heart by transmitting electrical signals from the distal end portion 14 of the catheter 1 to the monitor connected externally of the proximal end of the catheter. Thus, as shown in FIG. 3, in addition to electrode 15, three spaced apart ring electrodes 148 are disposed around the distal end portion 14. Pull wire 144 is anchored at its distal end to distal electrode 15. A conducting wire 147 is connected to distal electrode 15 and extends through inner tubes 142 and 142'. Separate conducting wires 145 are connected to each ring electrode 148 and extend outside of inner tubes 142 and 142'. The conducting wires 145, 147 extend through the entire length of central bore 104 and actuating mechanism 20, into plug connector 30 for connection to the external monitor. The ring electrodes 148 preferably range from 1 mm to 2 mm in width and are preferably spaced apart at a distance of approximately 1 cm. The distal electrode 15 preferably ranges from 1 mm to 5 mm in length.

A stiffening tube 162 (FIG. 3), having a bore 163, is disposed within central bore 104 of the outer tube 10 proximally to long inner tube 142 so that it frictionally engages central bore 104. Stiffening tube 162 is positioned proximal to junction 107, preferably at a distance of approximately 1 cm, and extends to proximal end portion 12 of outer tube 10, thereby providing increased rigidity to further restrict bending of the central and proximal end portions 12, 16 of outer tube 10. Bore 163 is dimensioned to allow passage therethrough of conducting wires 145, 147 and pull wire 144.

The actuating mechanism 20, depicted in FIGS. 1 and 2, comprises an actuating knob 201, a plunger 203 and a rubber stop 209, all of which are contained within a housing 205. Plunger 203 is disposed within bore 204 of a guide cap 207. Plunger housing 205 includes a threaded portion 206 that receives a mating threaded portion 208 of guide cap 207. Guide cap 207 has a central aperture extending therethrough to guide the axial movement of plunger 203. Pull wire 144 and conducting wires 145, 147, pass through the central aperture of guide cap 207 and bore 204 of plunger housing 205 and through a bore 210 in a rubber stop 209.

Plunger 203 is axially slidable within plunger housing 205. Rubber stop 209 is secured to the proximal end of the plunger 203 and frictionally engages the inner wall of the plunger housing 205 to control axial movement of plunger 203. Outward movement of plunger 203 is limited by guide cap 207 since its inner diameter is smaller than the outer diameter of plunger stop 203'.

Actuating knob 201 is secured at its proximal end to plunger 203 between the proximal end portion 12 of outer tube 10 and guide cap 207. The distal end of knob 201 is attached to the proximal end of tube 10 within a short protective sheath 206. Thus, movement of knob 201 causes simultaneous movement of plunger 203 and tube 10.

Plunger housing 205 further includes a retainer 214 to anchor the proximal end of pull wire 144. The proximal end of pull wire 144 is attached to a ball 217, which is housed within retainer 214 and its forward movement is restricted since its diameter is larger than the diameter of restricted passageway 219.

A second passageway 215, spaced from retainer 214, is formed in the rearmost portion of plunger housing 205 and is dimensioned to allow conducting wires 145 and 147 to pass from the plunger housing 205 into tubing 301 of plug connector 30.

An end cap 220 is attached to the rear portion of plunger housing 205. Cap 220 has a bore 221 cooperating with retainer 214 and an opening to receive tubing 301. Conducting wires 145 and 147 extend through tubing 301 and through socket 302 (FIG. 1) to link the electrodes of the catheter to an external monitor.

As is apparent from the description above, when catheter 1 is in its straight position shown in FIG. 1, actuating knob 201 is contiguous with front cap 207, and plunger 203 is in its inner position within plunger housing 205. To steer (bend) the catheter, actuating knob 201 is moved axially toward the distal end portion 14 of outer tube 10 in the direction of arrow A (FIG. 2), thereby causing displacement of the outer tube 10 as it moves forward relative to the anchored pull wire 144. The tension created by the pull wire 144 as it becomes taut causes the flexible distal end portion 14 of outer tube 10 to flex or bend. The direction of bending is limited by flat wire 146 which allows bending only in the direction normal to its width (perpendicular to the longitudinal axis of catheter 1). To return the distal end portion 14 to its original straight position of FIG. 1, the actuator bushing 201 is pulled back towards proximal end portion 12, reducing the tension on pull wire 144.

The catheter can be directed to any desired location by rotating the knob 201, which in turn causes corresponding rotation of the outer tube 10, and by sliding the bushing 201 distally to tension pull wire 144 to bend distal end portion 14.

The steerability of the catheter of the present invention advantageously enables the distal end portion 14 to access areas of the body which could not be reached by a non-bending catheter due to the presence of grooves, curves or narrow parts.

The catheter of the present invention can be inserted into a body through a femoral or brachial approach and has a variety of uses. In one application it is used for cardiac treatment and diagnostic procedures. One example of such cardiac use is to detect electrical signals inside the atrium of the heart, which are then sent to an external monitor. Another use of the catheter is for mapping the area of the heart valves to determine different areas of electrical activity. For example, the catheter can detect accessory pathways; i.e. improper pathways through which the signal is passing. The catheter can also be used for mapping electrical signals in the right or left ventricle to detect ectopic sites, e.g. areas where the ventricle is undesirably generating its own electric signals. These applications are mentioned by way of example only since there are additional uses of the catheter 1 of the present invention.

The soft distal end portion of the catheter increases the catheter's versatility since it can be used for exploratory purposes in areas of the body having thin walls, such as the coronary sinus, because, unlike catheters with stiff distal end portions, it will not puncture or otherwise damage these walls.

It is understood that the foregoing is considered as illustrative only of the principles of the invention. Therefore, within the scope of the appended claims, the invention may be practiced otherwise than as specifically described herein.

What is claimed is:

1. A steerable catheter comprising:
   a hollow outer tube having a distal end portion and a proximal end portion;
   a first inner tube disposed within said outer tube at said distal end portion;
   actuating means disposed adjacent said proximal end portion of said outer tube;
   a pull wire extending longitudinally from said actuating means to said distal end portion of said outer tube, said pull wire extending through said first inner tube;
   said actuating means being slidable towards said distal end portion for tensioning said pull wire to thereby bend said distal end portion of said outer tube; and
   a flat wire disposed within said outer tube parallel to said pull wire and secured to an outer surface of said first inner tube, said flat wire restricting the direction of bending of said distal end portion of said outer tube when said pull wire is tensioned.

2. A steerable catheter comprising:
   a hollow outer tube having a distal end portion and a proximal end portion;
   a first inner tube disposed within said outer tube at said distal end portion;
   actuating means disposed adjacent said proximal end portion of said outer tube;
   a pull wire extending longitudinally from said actuating means to said distal end portion of said outer tube, said pull wire extending through said first inner tube;
   said actuating means being slidable towards said distal end portion for tensioning said pull wire to thereby bend said distal end portion of said outer tube;
   a flat wire disposed within said outer tube parallel to said pull wire and secured to an outer surface of said first inner tube, said flat wire restricting the direction of bending of said distal end portion of said outer tube when said pull wire is tensioned; and
   a second inner tube spaced apart from and in coaxial alignment with said first inner tube, said second inner tube secured to said flat wire, and said pull wire extending through said second inner tube.

3. A steerable catheter as recited in claim 2, further comprising an electrode disposed at a tip of said distal end portion of said outer tube and a conducting wire extending from said electrode through said outer tube to a proximal end of the catheter.

4. A steerable catheter as recited in claim 3, further comprising a plurality of ring electrodes disposed within a wall of said outer tube at said distal end portion, and a conducting wire extending from each of said ring electrodes through said outer tube to said proximal end of said catheter.

5. A steerable catheter as recited in claim 2, further comprising a hollow stiffening tube disposed within said outer tube and extending from a central portion of said outer tube to said proximal end portion.

6. A steerable catheter as recited in claim 2, wherein an outer surface of said first and second inner tubes are secured to a surface of said flat wire.

7. A steerable catheter comprising:
   a hollow outer tube having a distal end portion and a proximal end portion;
   a first inner tube disposed within said outer tube at said distal end portion;
   actuating means disposed adjacent said proximal end portion of said outer tube;
   a pull wire extending longitudinally from said actuating means to said distal end portion of said outer tube, said pull wire extending through said first inner tube;
   said actuating means being slidable towards said distal end portion for tensioning said pull wire to thereby bend said distal end portion of said outer tube;
   a flat wire disposed within said outer tube parallel to said pull wire and secured to an outer surface of said first inner tube, said flat wire restricting the direction of bending of said distal end portion of said outer tube when said pull wire is tensioned;

said actuating means comprising a slidable plunger and an actuating bushing disposed between said plunger and said proximal end portion of said outer tube.

8. A steerable catheter as recited in claim 2, wherein a central and proximal end portion of said outer tube comprises a wire braid.

9. A steerable catheter as recited in claim 2, wherein said outer tube comprises a flexible tube at said distal end portion and a rigid tube having a wire braid embedded therein at a central and proximal portion, said rigid tube secured to said flexible tube in coaxial alignment with said flexible tube.

10. A steerable catheter as recited in claim 2, wherein said first and second inner tubes are composed of a flexible plastic material.

11. A steerable catheter as recited in claim 2, wherein a length of said first inner tube is greater than a length of said second inner tube.

12. A steerable catheter as recited in claim 11, wherein said outer tube comprises a reinforced portion and a flexible portion, said first inner tube extending both distal and proximal of a junction between said reinforced and flexible portions.

13. An electrode catheter having a proximal end portion and a distal end portion comprising means for bending said distal end portion of said catheter, said bending means comprising actuating means connected to said proximal end portion and a pull wire extending from said actuating means to said distal end portion, said actuating means slidable axially of said catheter to a distal position to tension said pull wire to bend said distal end portion, said pull wire extending through first and second coaxially aligned and axially spaced inner tubes disposed within said catheter at said distal end portion.

14. An electrode catheter having a proximal end portion and a distal end portion comprising means for bending said distal end portion of said catheter, said bending means comprising actuating means connected to said proximal end portion and a pull wire extending from said actuating means to said distal end portion, said actuating means slidable axially of said catheter to a distal position to tension said pull wire to bend said distal end portion, said pull wire extending through first and second coaxially aligned inner tubes disposed within said catheter at said distal end portion, and a longitudinally extending flat wire disposed parallel to said pull wire and secured to an outer surface of said first and second inner tubes to limit the direction of bending of said distal end portion of said catheter.

15. A steerable catheter as recited in claim 14, wherein said first inner tube has a length greater than the length of said second inner tube.

16. A steerable catheter as recited in claim 15, wherein said first and second inner tubes are composed of a flexible plastic material.

17. A steerable catheter as recited in claim 16, wherein said second inner tube is positioned proximally of said first inner tube and is spaced from a distal tip of the catheter.

18. A steerable catheter as recited in claim 17, wherein said catheter comprises an outer tube having a flexible portion at said distal end portion and a rigid portion at said proximal end portion.

19. A steerable catheter as recited in claim 18, further comprising a longitudinally extending stiffening tube disposed inside said catheter proximally of said distal end portion.

* * * * *